United States Patent
Kast et al.

(10) Patent No.: US 7,402,083 B2
(45) Date of Patent: Jul. 22, 2008

(54) MEDICAL ELECTRICAL LEAD CONNECTION SYSTEMS AND METHODS

(75) Inventors: John Kast, Hugo, MN (US); Mark Lent, Brooklyn Park, MN (US); Jim Olsen, Plymouth, MN (US); Andrew Ries, Lino Lakes, MN (US); James Skakoon, St. Paul, MN (US); Carl Wahlstrand, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/689,531

(22) Filed: Mar. 22, 2007

(65) Prior Publication Data
US 2008/0009192 A1  Jan. 10, 2008

Related U.S. Application Data

(60) Provisional application No. 60/785,194, filed on Mar. 23, 2006.

(51) Int. Cl.
H01R 24/00 (2006.01)
(52) U.S. Cl. .................................. 439/660; 439/909
(58) Field of Classification Search ............. 439/660, 439/909, 668
See application file for complete search history.

(56) References Cited

U.S. PATENT DOCUMENTS

| | | |
|---|---|---|
| 4,469,104 A | 9/1984 | Peers-Trevarton |
| 4,712,557 A | 12/1987 | Harris |
| 4,869,255 A | 9/1989 | Putz |
| 5,354,326 A | 10/1994 | Comben et al. |
| 5,560,358 A | 10/1996 | Arnold et al. |
| 6,162,101 A | 12/2000 | Fischer et al. |
| 6,321,126 B1 | 11/2001 | Kuzma |
| 6,415,168 B1 | 7/2002 | Putz |
| 6,575,793 B1 * | 6/2003 | Li et al. ...................... 439/668 |
| 6,662,035 B2 | 12/2003 | Sochor |
| 6,725,096 B2 | 4/2004 | Chinn et al. |
| 6,741,892 B1 | 5/2004 | Meadows et al. |
| 7,134,919 B2 | 11/2006 | Putz |

* cited by examiner

Primary Examiner—Renee S Luebke
Assistant Examiner—Vanessa Girardi
(74) Attorney, Agent, or Firm—Elisabeth Lacy Belden; Rick L. Franzen

(57) ABSTRACT

An electrical connection assembly of a medical device includes at least one conductive sidewall mounted in a fixed position to a module base; the sidewall may be electrically coupled to a feedthrough wire. The assembly further includes at least one resilient member to apply a spring force against a connector element of a lead connector when the connector element is positioned adjacent to the conductive sidewall. The spring force of the resilient member causes electrical coupling between the connector element and the conductive sidewall.

40 Claims, 6 Drawing Sheets

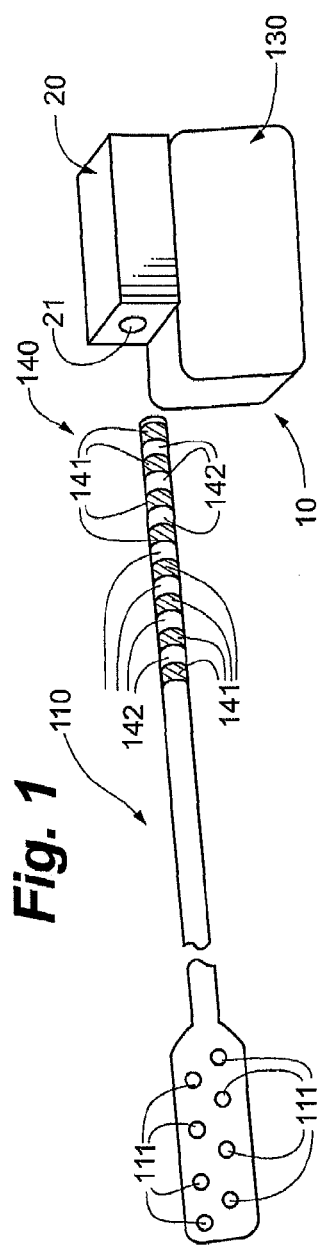
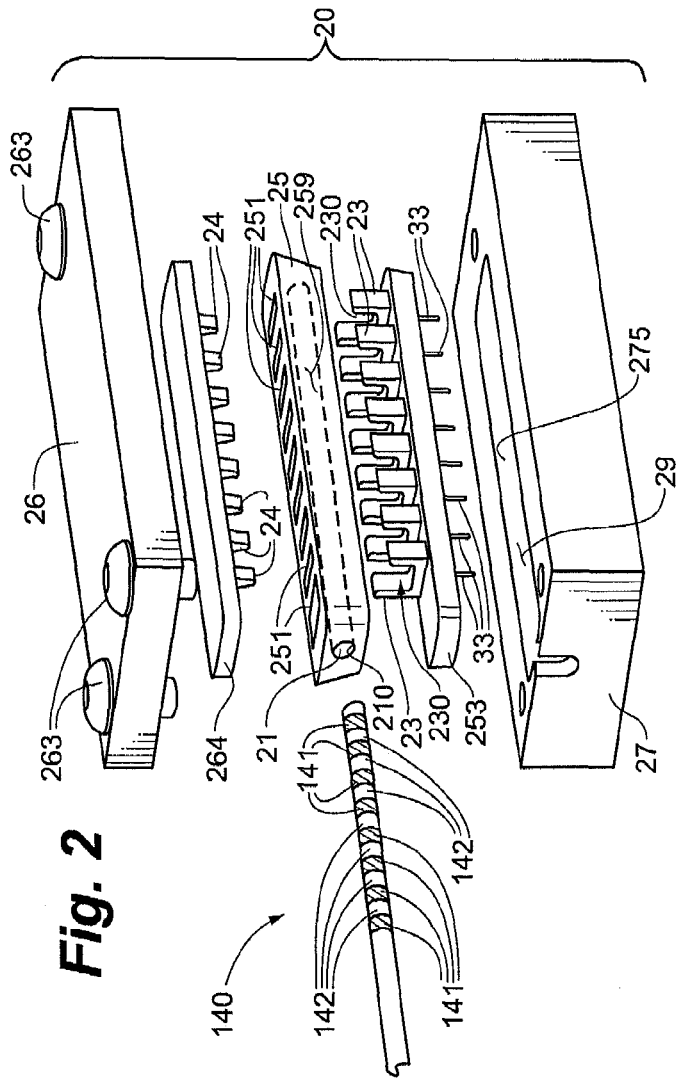

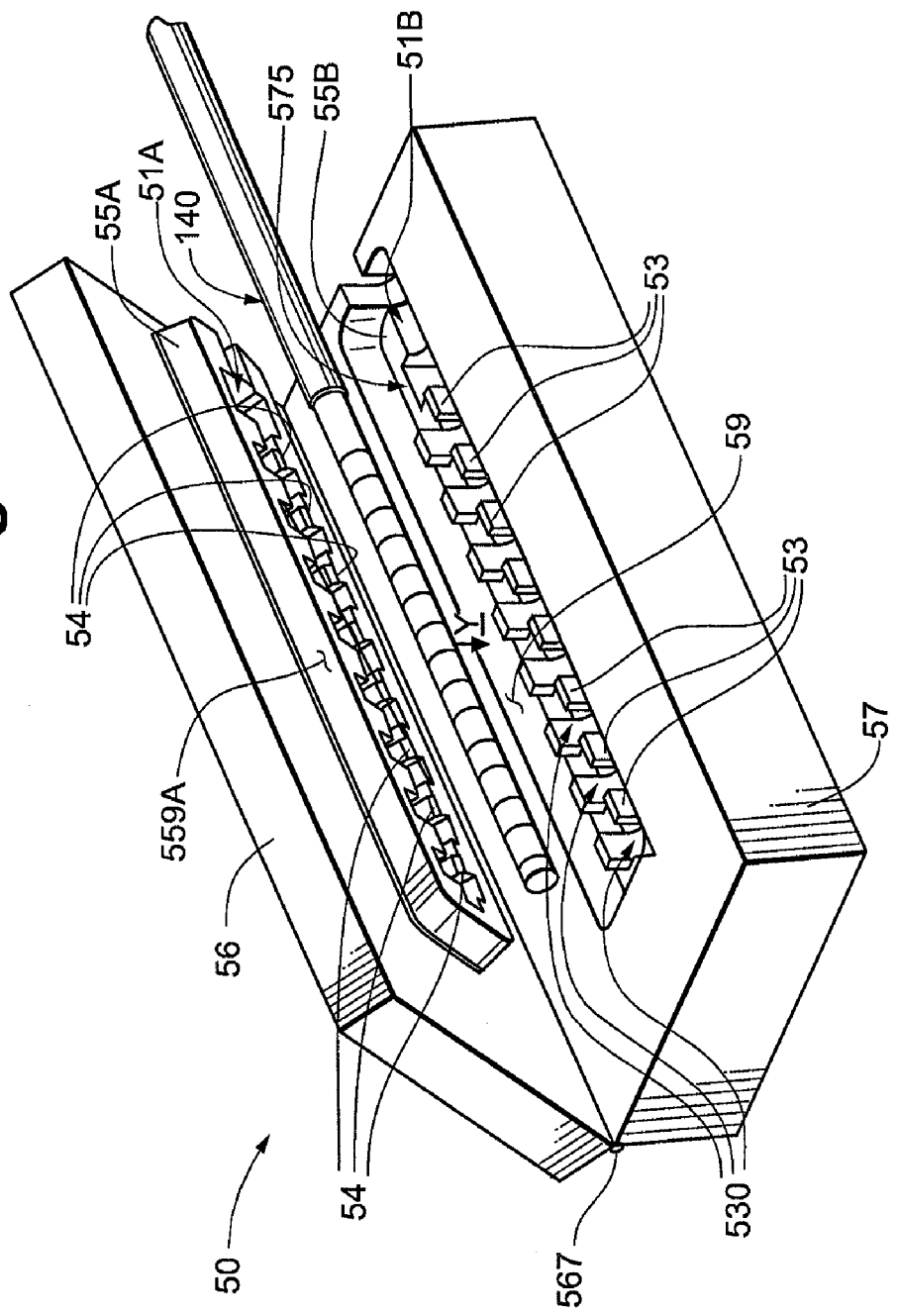

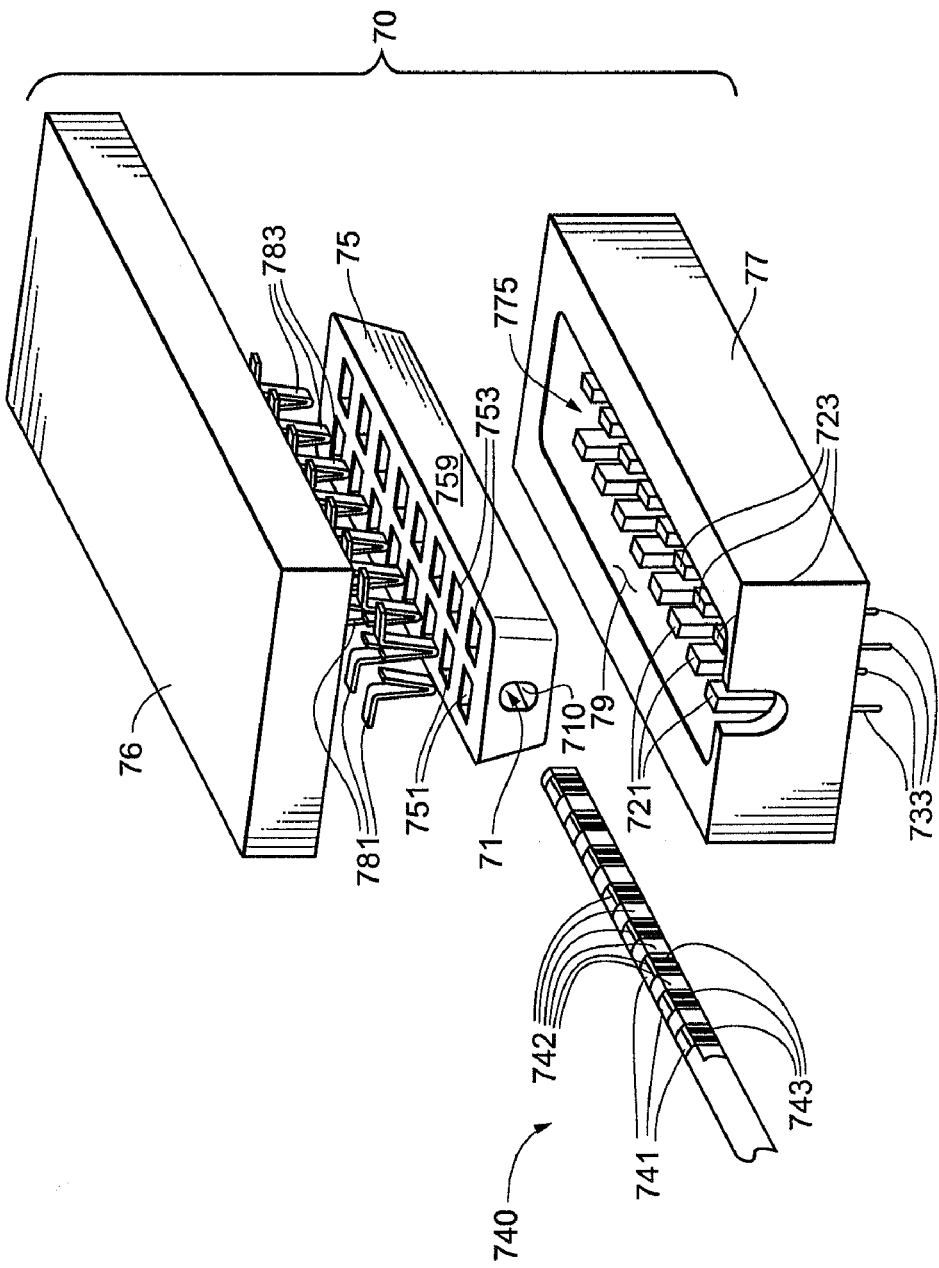

MEDICAL ELECTRICAL LEAD CONNECTION SYSTEMS AND METHODS

RELATED APPLICATION

This application claims priority to U.S. provisional application, Ser. No. 60/785,194, which was filed on Mar. 23, 2006, and which is hereby incorporated by reference, in its entirety.

TECHNICAL FIELD

The present invention pertains to electrical connection systems, or assemblies, and methods, and more particularly to assemblies and methods facilitating electrical connections of medical electrical leads to medical devices.

BACKGROUND

A host of medical devices include electrical connection assemblies for coupling with a type of medical electrical lead connector that is formed along a proximal portion of the lead and includes a plurality of connector elements disposed along a length thereof.

These assemblies typically include a plurality of electrical contacts positioned within an area, or bore, of what is typically called a connector module, or header, at locations corresponding to the connector elements of the lead connector, in order to mate with the corresponding connector elements when the connector is inserted within the bore. Some device connection assemblies further include sealing elements located between the electrical contacts to mate with insulative spacers located between the connector elements of the lead connector, and thereby provide electrical isolation between each mating contact and connector element. Although a variety of connector assembly configurations are known in the art, there is still a need for new methods and assembly designs that provide stable electrical connections, and isolation therebetween, without increasing a force necessary to insert lead connectors into the assembly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 1 is a perspective view of a portion of an exemplary medical device system, according to some embodiments of the present invention.

FIG. 2 is an exploded perspective view of an electrical connection assembly, according to some embodiments of the present invention.

FIG. 5 is a perspective view of an electrical connection assembly, according to some alternate embodiments of the present invention, in an open position.

FIG. 7 is an exploded perspective view of an electrical connection assembly, according to yet further embodiments of the present invention.

DETAILED DESCRIPTION

Figure 3A:
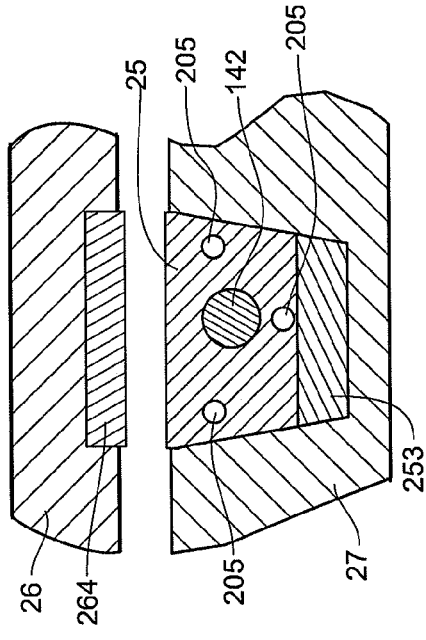
FIG. 3A is a cross-section, axial view through an electrical contact portion of the assembly shown in FIG. 2, according to some embodiments, in an open position.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

FIG. 1 is a perspective view of a portion of an exemplary medical device system 10, according to some embodiments of the present invention. FIG. 1 illustrates system 10 including a medical electrical lead 110 and a medical device 100; a connector 140 of lead 110 is shown terminating a proximal end thereof and including a plurality of connector elements 141 spaced apart along a length of connector 140 by a plurality of insulative spacers 142. Materials and construction methods for lead connectors, such as connector 140 (as well as connector 740, described below), are well known to those skilled in the art. FIG. 1 further illustrates device 100 including a housing 130 and an electrical connection assembly 20, wherein assembly 20 is mounted to housing 130 and includes an area, or bore 21 into which lead connector 140 may be inserted for electrical coupling with circuitry contained within housing 130. FIG. 2 is an exploded perspective view of electrical connection assembly 20, according to some embodiments of the present invention. FIG. 2 illustrates assembly 20 including a module cap 26, a module base 27, a plurality of rigid contact blocks 23 projecting from a foundation 253, a plurality of resilient members 24 projecting from a plate 264, and a bulk sealing member 25 including an interior surface 210 defining a portion of a perimeter of bore 21. Although FIG. 2 shows plate 264 independent of cap 26, it should be noted that plate 264 may be integrally formed with cap 26, or members 24 directly mounted to cap 26. Likewise foundation 253 for blocks 23 may be integral with base 27; however, if base 27 is formed from a conductive material, foundation 253, being formed from a non-conductive material, may be necessary to provide electrical isolation between each of blocks 23. FIG. 2 further illustrates a plurality of feedthrough wires 33, each of which are coupled to a corresponding contact block 23; exemplary materials for wires 33 include, without limitation, tantalum, platinum-iridium (Pt/IR) and niobium. Those skilled in the art will appreciate that, if device 100 is an implantable device, device housing 130 includes a hermetically sealed feedthrough port for each feedthrough wire 33.

According to the illustrated embodiment, base 27 includes a cavity 275 for holding sealing member 25 and blocks 23, wherein each block 23, for example, formed from MP35N, Pt/IR, titanium or stainless steel, is mounted in a fixed position within base 27 and extends into a corresponding opening 251 of sealing member 25 such that a groove 230 of each block 23 further defines the perimeter of bore 21, and such that sealing member 25 extends around each block 23 within cavity 275. When cap 26 is brought alongside base 27, each resilient member 24 also extends into a corresponding opening 251 of sealing member 251, for example as is illustrated in FIG. 3A. According to preferred embodiments of the present invention, sealing member 25 is formed from an elastomeric insulative material, preferably silicone rubber, and is held in cavity 275, for example, via an interference fit, without additional securing means, for example, bonding; however the scope of the invention is not so limited, and additional securing means, for example, silicone or polyurethane adhesive, may be used to retain member 25 in cavity 275, according to alternate embodiments.

Figure 3B:
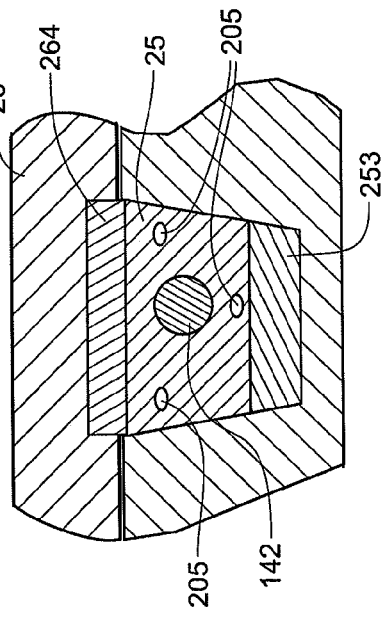
FIG. 3B is a cross-section, axial view through a non-contact portion of the assembly shown in FIG. 2, according to some embodiments, in an open position.
Figure 4A:
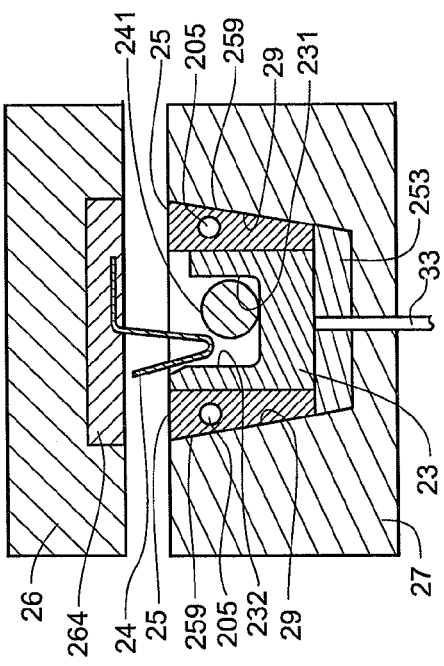
FIG. 4A is a cross-section, axial view through an electrical contact portion of the assembly shown in FIG. 2, according to some embodiments, in a closed position.

FIGS. 3A-B are cross-section, axial views through an electrical contact portion at a location of one of sealing member openings 251, and through a non-contact portion of assembly 20, for example, between two of sealing member openings 251, respectively, according to some embodiments, both with cap 26 in an open position, and both with connector 140 having been axially inserted therein, for example, via arrow A of FIG. 1. FIG. 3A illustrates one of connector elements 141 located within groove 230 of the corresponding block 23, and FIG. 3B illustrates one of insulative spacers 142 located within a portion of bore 21 defined by interior surface 210 of sealing member 25. FIG. 3A further illustrates block 23 including a first sidewall 231 on a first side of groove 230 and a second sidewall 232 on a second side of groove 230; according to the illustrated embodiment, each sidewall 231 is conductive for electrical coupling of the corresponding connector element 141 to the corresponding feedthrough wire 33, when connector 140 is fully inserted within bore 21 such that each connector element 141 is located alongside first groove sidewall 231 of the corresponding block 23. Sidewall 231 may include a surface treatment to enhance surface conductivity, for example, gold sputtering or electroplating, according to some embodiments. When each resilient member 24 is pressed into the corresponding groove 230, alongside the corresponding connector elements 141, for example as illustrated in FIG. 4A, each connector element 141 is forced into electrical contact with conductive sidewall 231 of the corresponding contact block 23. It should be noted that resilient member 24, for example formed as a spring clip, may be conductive, for example, formed from stainless steel, or nonconductive, for example, formed from a polymer coated metal or a creep-resistant resilient plastic, such as PEEK, since members 24 are not required to be conductive in order to facilitate electrical coupling between connector elements 141 and corresponding contact blocks 23 of the illustrated embodiment.

Figure 4B:
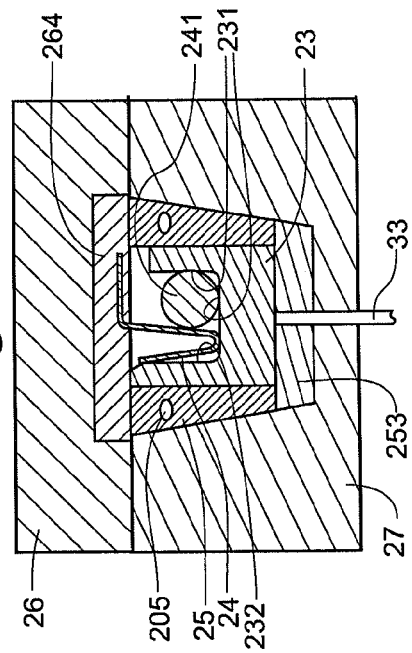
FIG. 4B is a cross-section, axial view through a non-contact portion of the assembly shown in FIG. 2, according to some embodiments, in a closed position.

FIGS. 4A-B are cross-section, axial views, similar to FIGS. 3A-B, but with cap 26 in a closed, or fully engaged position, for example, being secured to base 27 by screws 263 (FIG. 2). With reference back to FIGS. 3A-B, it will be appreciated that, when cap 26 is not fully engaged with base 27, assembly 20 provides sufficient clearance for relatively easy axial insertion of connector 140 into bore 21. FIG. 4A illustrates resilient member 24 being compressed between connector element 241 and groove sidewall 232, thereby applying a spring force that holds connector element 141 against conductive sidewall 231 for stable contact therebetween; and FIG. 4B illustrates the portion of bore 21 defined by interior surface 210 of seal member 25 compressed about insulative spacer 142 to provide electrical isolation between adjacent mating connector elements 141 and contact blocks 23. With reference back to FIG. 1, those skilled in the art will appreciate that an insulated conductor extending within lead 110 electrically couples each connector element 141 to a corresponding electrode 111 so that, when each connector element 141 is coupled, for example, as shown in FIG. 3A, to the corresponding contact block 23, each electrode 111 is electrically coupled to the circuitry contained in device housing 130.

FIGS. 3A-B and 4A-B further illustrate opposing tapered sidewalls 29 of cavity 275 interfacing with tapered outer surfaces 259 of sealing member 25. The interface of corresponding tapers 29, 259 may reduce the force and displacement required to compress sealing member 25 in order to achieve adequate sealing about insulative spacers 142 of lead connector 140, and may further prevent significant distortion of those portions of bore 21 defined by interior surface 210 of sealing member 25. With further reference to FIGS. 3A-B and 4A-B, optional voids 205 are shown formed in sealing member 25; the inclusion of voids 205 in sealing member 25 can allow a volumetric tolerance of member 25 to be opened up, for example, by providing some additional compressible space in a bulk volume thereof, thus, if the bulk volume of sealing member 25 exceeds that of cavity 275, voids 205 can be compressed to effectively reduce the bulk volume of member 25, when cap 26 being is fully engaged with base 27. It should be noted that voids 205 may alternately be located along exterior surfaces of sealing member 25, for example, in the form of grooves extending along sides 259. It should be understood that optional voids 205 are macroscopic and discretely placed by design, as opposed to microscopic and randomly dispersed voids, which might be characteristic of a particular elastomeric material employed by embodiments of the present invention; however, alternate embodiments of the present invention can employ elastomeric materials having microscopic and randomly dispersed voids to provide the compressible space.

FIG. 5 is a perspective view of an electrical connection assembly 50, according to some alternate embodiments of the present invention, in an open position to receive a radial, or sideways insertion, for example, via arrow Y, of lead connector 140. FIG. 5 illustrates assembly 50 including a first bulk sealing member 55A and a plurality of resilient members 54 attached to a cap portion 56, and a second bulk sealing member 55B and a plurality of contact blocks 53 held within a cavity 575 of a base portion 57. Like contact blocks 23 of assembly 20, each contact block 53 includes a groove 530, which defines a portion of a perimeter of an area into which lead connector 140 is inserted, per arrow Y. FIG. 5 further illustrates cap 56 attached to base 57 via a hinged coupling 567. When cap 56 is closed over base 57, first sealing member 55A mates with second sealing member 55B and an interior surface 51A of first member 55A combines with an interior surface 55B of second member to define a portion of a bore similar to bore 21 of assembly 20. Like sealing member 25, first and second sealing members 55A,B are formed from an elastomeric insulative material, preferably silicone rubber, and second sealing member 55B is fitted and held within cavity 575 without need for additional securing means, such as bonding, although the scope of the present invention does not preclude additional securing means. First sealing member 55A may be attached to cap 56 by bonding, for example with a silicone or polyurethane adhesive.

Figure 6B:
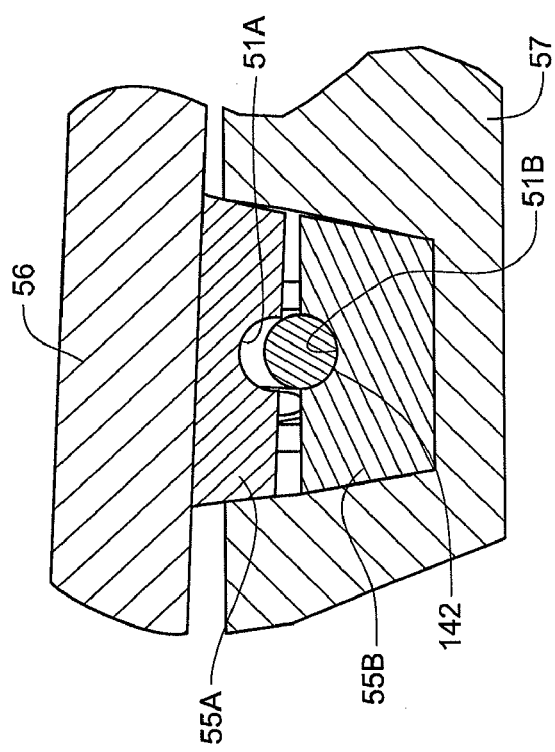
FIG. 6B is a cross-section, axial view through a non-contact portion of the assembly shown in FIG. 5, according to some embodiments.
Figure 6A:
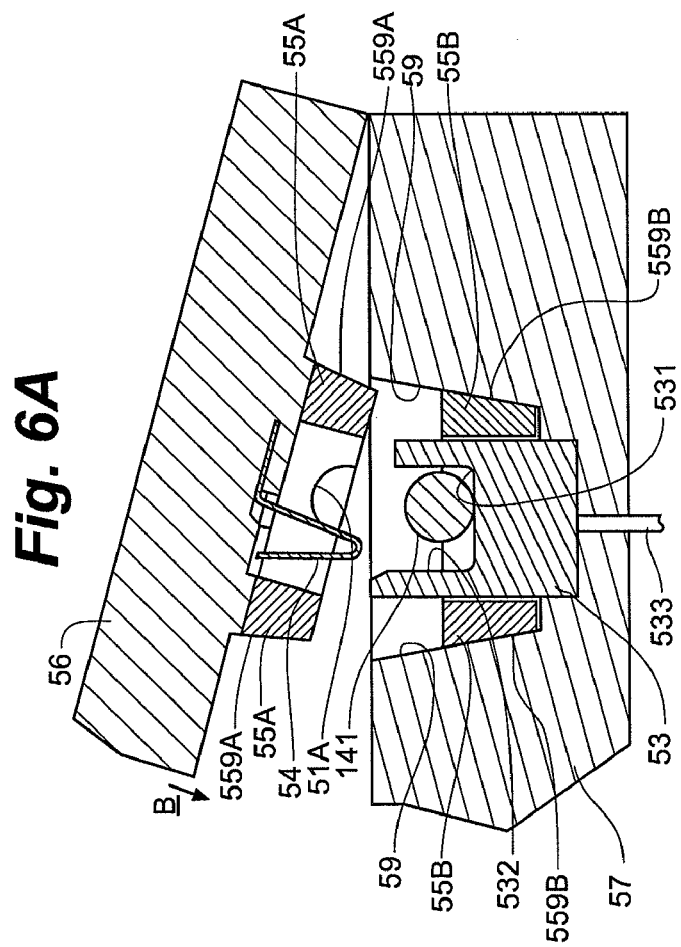
FIG. 6A is a cross-section, axial view through an electrical contact portion of the assembly shown in FIG. 5, according to some embodiments.

FIG. 6A is a cross-section, axial view through an electrical contact portion of assembly 50, according to some embodiments; and FIG. 6B is a cross-section, axial view through a non-contact portion of assembly 50, according to some embodiments. FIG. 6A illustrates one of connector elements 141 of lead connector 140 located in groove 530 of the corresponding contact block 53 and resilient member 54, very similar to member 24 of assembly 20, being brought down, by the closing of cap 56, per arrow B, to be pressed into groove 530, alongside connector element 141, for example, similar to assembly 20, as illustrated in FIG. 4A. As with assembly 20, each connector element 141 is forced into relatively stable electrical contact with a conductive sidewall 531 of the corresponding contact block groove 530 by a spring force of corresponding resilient member 54 being compressed between connector element 141 and an opposing sidewall 532 of groove 230. Resilient member 54 may be formed from any of the materials previously presented for resilient member 24 of assembly 20. FIG. 6A further illustrates one of a plurality of feedthrough wires 533 coupled to contact block 53, and, it should be understood that each contact block 53 is coupled to one of wires 533, similar to blocks 23 and wires 33 of assembly 20, and that blocks 53 and wires 533 may be formed of any of the materials presented for blocks 23 and wires 33, respectively, of assembly 20. FIGS. 6A-6B further illustrate cavity 575 of base 57 including opposing tapered sidewalls 59 to interface with corresponding outer tapered surfaces 559A, B of sealing members 55A,B, which interface may reduce the force and displacement required to compress seal members 55A,B in order to achieve adequate sealing about insulative spacers 142 of lead connector 140. Although not shown, one or both of sealing members 55A,B may include one or more voids formed therein to alleviate volumetric tolerance constraints, as previously described for member 25.

FIG. 7 is an exploded perspective view of an electrical connection assembly 70, according to yet further embodiments of the present invention, and a corresponding lead connector 740. FIG. 7 illustrates assembly 70 including a cap 76, a base 77, a first column of rigid contact blocks 721, a second column of rigid contact blocks 723 extending alongside the first column, a first column of resilient members 781, a second column of resilient members 783 extending alongside the first column, and a bulk sealing member 75 including an interior surface 710 defining a portion of a perimeter of a bore 71 into which connector 740 may be inserted. Each of resilient members 781, 783 may be a spring clip formed from a conductive material such as stainless steel, Pt/IR, titanium, or MP35N. Likewise rigid contact blocks 721, 723 may be formed from stainless steel, Pt/IR, titanium or MP35N. According to the illustrated embodiment, base 77 includes a cavity 775 for holding blocks 721, 723; each block 721 extends into a corresponding opening 751 of sealing member 75, and each block 723 into a corresponding opening 753 of sealing member 75, so that sealing member 75 extends around each block 721, 723, within cavity 275, and an inner sidewall 701, 703 of each block 721, 723 further defines bore 71.

Figure 8:
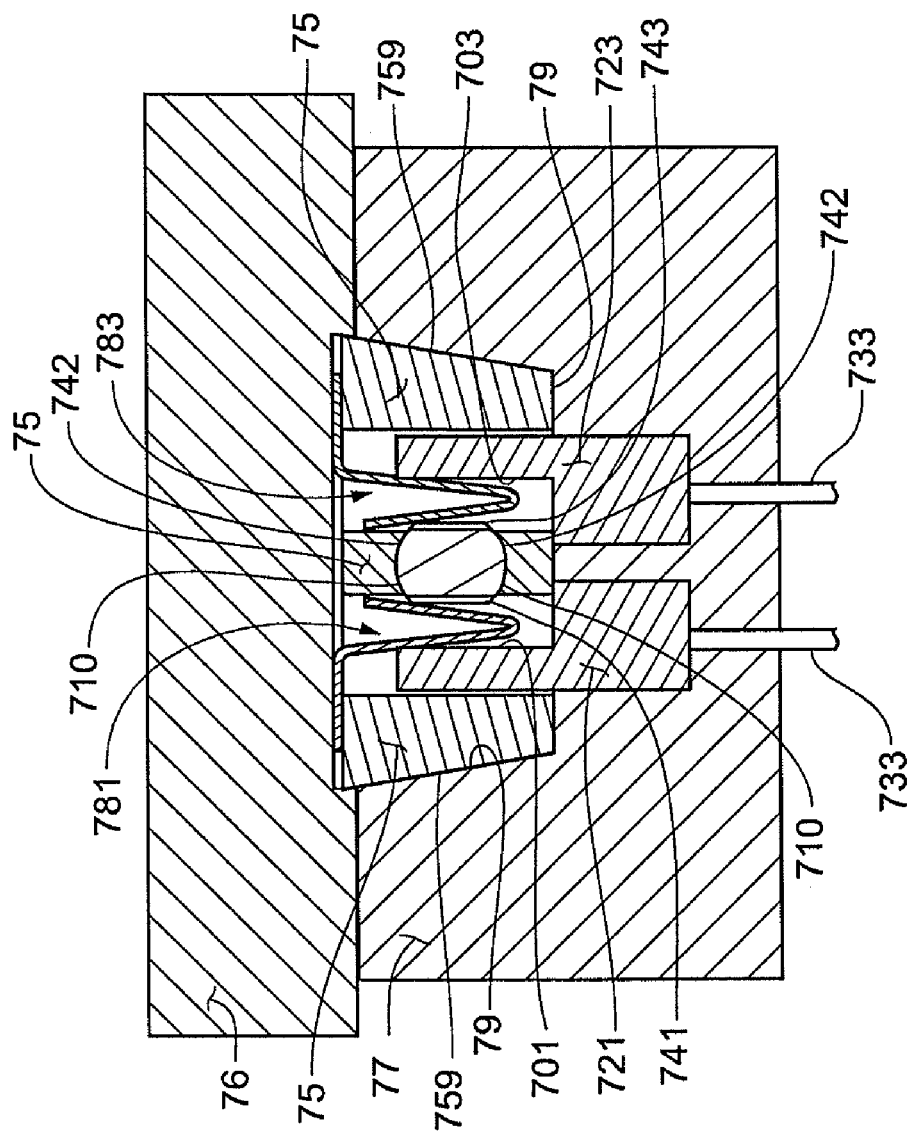
FIG. 8 is a cross-section, axial view through an electrical contact portion of the assembly shown in FIG. 7, according to some embodiments.

FIG. 8 is a cross-section, axial view through an electrical contact portion of assembly 70 at one pair of openings 751, 753, according to some embodiments, wherein connector 740 has been inserted into bore 71 for electrical coupling. FIG. 8 illustrates a feedthrough wire 733, for example, formed from any of the materials previously presented for wires 33, coupled to each of blocks 721, 723; it should be understood that, each of a plurality of wires 733 are coupled to corresponding blocks 721, 723 included in assembly 70. FIGS. 7 and 8 further illustrate connector 741 having what may be designated as a "segmented" construction, wherein a first column of connector elements 741 and a second column of connector elements 743 are spaced apart from one another one either side of a longitudinal axis of connector 741; insulative spacers 742 are shown extending between each column to isolate connector elements 741 from connector elements 743 and between each connector element 741, 743 within each column to isolate the elements in each column from one another. Although surfaces of connector elements 741, 743 are shown being relatively flat, it should be understood that the scope of the present invention is not so limited, and that, according to alternate embodiments, surfaces of elements 741, 743 are curved, for example, extending along a circumference of connector 740.

According to the illustrated embodiment, when cap 76 of assembly 70 is brought into engagement with base 77, each of resilient members 781 is inserted into the corresponding seal member opening 751 and each of resilient members 783 is inserted into the corresponding seal member opening 753 such that each member 781 is compressed between inner sidewall 701 of the corresponding block 721 and the corresponding connector element 741, and each member 783 is compressed between inner sidewall 703 of the corresponding block 723 and the corresponding connector element 743. Thus, when cap 76 is securely engages with base 77, a spring force of each resilient member 781, 783 causes relatively stable electrical coupling between the corresponding connector element 741, 743 and the corresponding sidewall 701, 703, via conductive surfaces of each corresponding resilient member 781, 783. These surfaces of members 781, 783, as well as sidewalls 701, 703, may include surface treatments to enhance conductivity, for example, gold sputtering or electroplating.

FIG. 8 further illustrates opposing tapered sidewalls 79 of cavity 775 interfacing with opposing tapered outer surfaces 759 of sealing member 75, similar to that for assembly 20. Sealing member 75, like sealing member 25 of assembly 20, is formed from an elastomeric insulative material, preferably silicone rubber, an may be retained in cavity 775 without additional securing means. Furthermore, like sealing member 25, although not shown, sealing member 75 may include one or more voids formed therein to alleviate volumetric tolerance constraints, as previously described for member 25. With reference to FIGS. 7 and 8, it will be appreciated that sealing member 75 surrounds each of resilient members 781, 783 and blocks 721,723 and interfaces with insulative spacers 742 of connector 740 to provide electrical isolation, when cap 76 is fully engaged with base 77, between each electrical coupling of connector element 741, 743 to corresponding contact block sidewall 701, 703, via corresponding resilient member 781, 783.

In the foregoing detailed description, the invention has been described with reference to specific embodiments. However, it may be appreciated that various modifications and changes can be made without departing from the scope of the invention as set forth in the appended claims.

We claim:

1. An electrical connection assembly for a medical device, the assembly comprising:

a module including a base for mounting to a housing of the medical device, a cap engagable with the base, and an area for receiving a medical electrical lead connector, the lead connector including a plurality of connector elements;

a plurality of rigid conductive sidewalls each mounted in a fixed position to the module base, each sidewall defining a portion of a perimeter of the area for receiving the lead connector;

a plurality of feedthrough wires each coupled to a corresponding sidewall of the plurality of rigid conductive sidewalls and each extending from the assembly for electrical coupling with circuitry contained within the housing of the medical device; and a plurality of resilient members attached to the module cap, each member applying a spring force against a corresponding connector element of the plurality of connector elements, when the lead connector is received within the area, when each connector element of the plurality of connector elements is positioned adjacent to a corresponding conductive sidewall of the plurality of conductive sidewalls, and when the module cap is engaged with the module base;

wherein the applied spring force of each resilient member causes electrical coupling between the corresponding connector element and the corresponding conductive sidewall.

2. The assembly of claim 1, wherein:

the plurality of connector elements comprises a first connector element and a second connector element, the first and second connector elements spaced apart from one another along a length of the lead connector; and the plurality of rigid conductive sidewalls comprises a first sidewall and a second sidewall, the first and second sidewalls spaced apart from one another for alignment with the first and second connector elements, respectively, when the lead connector is received within the area.

3. The assembly of claim 1, wherein:

the plurality of connector elements comprises a first connector element and a second connector element, the first and second connector elements spaced apart from one another on either side of a longitudinal axis of the lead connector; and the plurality of rigid conductive sidewalls comprises a first sidewall and a second sidewall, the first and second sidewalls disposed opposite one another for alignment with the first and second connector elements, respectively, when the lead connector is received within the area.

4. The assembly of claim 1, wherein the spring force of each resilient member urges the corresponding connector element into contact with the corresponding conductive sidewall to cause the electrical coupling.

5. The assembly of claim 1, wherein each resilient member further includes a conductive surface and the spring force of each resilient member urges the conductive surface of the member into contact with the corresponding connector element and the corresponding conductive sidewall to cause the electrical coupling.

6. The assembly of claim 1, wherein the module further includes a hinged coupling joining the module cap to the module base.

7. The assembly of claim 1, further comprising a sealing member surrounding the plurality of conductive sidewalls and including at least one interior surface further defining the perimeter of the area for receiving the lead connector.

8. The assembly of claim 7, wherein:

the sealing member further includes opposing outer tapered surfaces; and the module base includes a cavity having opposing tapering sidewalls interfacing with the outer tapered surfaces of the sealing member.

9. The assembly of claim 7, wherein the sealing member further includes a first portion attached to the module cap and surrounding the plurality of resilient members, and a second portion held in the module base.

10. The assembly of claim 9, wherein:

the first and second portions of the sealing member each include opposing outer tapered surfaces; and the module base includes a cavity having opposing tapering sidewalls interfacing with the outer tapered surfaces of the first and second portions of the sealing member.

11. A medical device, comprising:

a housing containing electronic circuitry;

a module including a base mounted to the housing, a cap engagable with the base, and an area for receiving a medical electrical lead connector, the lead connector including a plurality of connector elements;

a plurality of feedthrough wires each extending from the module and into the housing for electrical coupling with the circuitry contained therein;

a plurality of rigid conductive sidewalls each mounted in a fixed position to the module base, each defining a portion of a perimeter of the area for receiving the lead connector, and each being electrically coupled to a corresponding feedthrough wire of the plurality of feedthrough wires; and a plurality of resilient members attached to the module cap, each member applying a spring force against a corresponding connector element of the plurality of connector elements, when the lead connector is received within the area, when each connector element of the plurality of connector elements is positioned adjacent to a corresponding conductive sidewall of the plurality of conductive sidewalls, and when the module cap is engaged with the module base;

wherein the applied spring force of each resilient member causes electrical coupling between the corresponding connector element and the corresponding conductive sidewall.

12. The device of claim 11, wherein:

the plurality of connector elements comprises a first connector element and a second connector element, the first and second connector elements spaced apart from one another along a length of the lead connector; and the plurality of rigid conductive sidewalls comprises a first sidewall and a second sidewall, the first and second sidewalls spaced apart from one another for alignment with the first and second connector elements, respectively, when the lead connector is received within the area.

13. The device of claim 11, wherein:

the plurality of connector elements comprises a first connector element and a second connector element, the first and second connector elements spaced apart from one another on either side of a longitudinal axis of the lead connector; and the plurality of rigid conductive sidewalls comprises a first sidewall and a second sidewall, the first and second sidewalls disposed opposite one another for alignment with the first and second connector elements, respectively, when the lead connector is received within the area.

14. The device of claim 11, wherein the spring force of each resilient member urges the corresponding connector element into contact with the corresponding conductive sidewall to cause the electrical coupling.

15. The device of claim 11, wherein each resilient member further includes a conductive surface and the spring force of each resilient member urges the conductive surface of the member into contact with the corresponding connector element and the corresponding conductive sidewall to cause the electrical coupling.

16. The device of claim 11, wherein the module further includes a hinged coupling joining the module cap to the module base.

17. The device of claim 11, further comprising a sealing member surrounding the plurality of conductive sidewalls and including at least one interior surface further defining the perimeter of the area for receiving the lead connector.

18. The device of claim 17, wherein:
the sealing member further includes opposing outer tapered surfaces; and
the module base includes a cavity having opposing tapering sidewalls interfacing with the outer tapered surfaces of the sealing member.

19. The device of claim 17, wherein the sealing member further includes a first portion attached to the module cap and surrounding the plurality of resilient members, and a second portion held in the module base.

20. The device of claim 19, wherein:
the first and second portions of the sealing member each include opposing outer tapered surfaces; and
the module base includes a cavity having opposing tapering sidewalls interfacing with the outer tapered surfaces of the first and second portions of the sealing member.

21. A method for making an electrical connection between a connector of a medical electrical lead and a rigid conductive sidewall held fixed within a connector module of a medical device, the method comprising:
bringing a connector element of the lead connector into proximity with the rigid conductive sidewall; and
applying a spring force against the connector element, after bringing the element into proximity with the sidewall, by bringing a resilient member into contact with the connector element, the spring force causing electrical coupling between the connector element and the conductive sidewall.

22. The method of claim 21, wherein bringing the connector element into proximity with the rigid conductive sidewall comprises inserting the lead connector axially into a bore of the connector module, wherein a portion of a perimeter of the bore is defined by the sidewall.

23. The method of claim 21, wherein bringing the connector element into proximity with the rigid conductive sidewall comprises inserting the lead connector radially into an area of the connector module, wherein a portion of a perimeter of the area is defined by the sidewall.

24. The method of claim 21, wherein bringing the resilient member into contact with the connector element comprises engaging a cap of the connector module with a base of the connector module, wherein the resilient member is attached to the cap.

25. The method of claim 21, wherein the spring force applied to the connector element forces the connector element into contact with the rigid conductive sidewall to cause the electrical coupling.

26. The method of claim 21, wherein the spring force applied to the connector element forces the resilient member into contact with the rigid conductive sidewall, to cause the electrical coupling.

27. An electrical connection assembly for a medical device, the assembly comprising:
a base for mounting to a housing of the device, the base including a cavity having opposing tapering sidewalls;
a cap engagable with the base;
an area for receiving a medical electrical lead connector, the lead connector including a plurality of connector elements;
a plurality of electrical contact surfaces held within the cavity, each contact surface of the plurality of contact surfaces defining a portion of a perimeter of the area for receiving the lead connector, and each contact surface located for electrical coupling with a corresponding connector element of the lead connector, when the lead connector is inserted within the area; and
a sealing member held within the base cavity and surrounding the plurality of electrical contact surfaces, the sealing member including at least one interior surface, forming another portion of the perimeter of the area for receiving the lead connector, and opposing outer tapered surfaces interfacing with the opposing tapering sidewalls of the cavity;
wherein, when the cap is engaged with the base, the at least one interior surface of the sealing member is compressed about the lead connector inserted within the area.

28. The assembly of claim 27, wherein the at least one interior surface of the sealing member surrounds a bore, the bore forming a portion of the area for receiving the lead connector.

29. The assembly of claim 27, wherein the sealing member further includes a plurality of openings, and each contact surface extends into a corresponding opening of the plurality of openings.

30. The assembly of claim 29, wherein the plurality of contact surfaces are arranged in first and second columns, the first and second columns extending alongside one another.

31. The assembly of claim 29, wherein the sealing member further includes at least one void, independent of the at least one interior surface and the plurality of openings of the sealing member, the at least one void providing compressible space in a bulk volume of the sealing member.

32. The assembly of claim 27, further comprising another sealing member attached to the cap, the other sealing member including at least one interior surface further defining the area for receiving the lead connector and the other sealing member configured to mate with the sealing member held in the base cavity, when the cap is engaged with the base.

33. The assembly of claim 32, wherein the other sealing member includes opposing outer tapered surfaces interfacing with the opposing tapering sidewalls of the cavity, when the cap is engaged with the base.

34. A medical device, comprising:
a housing containing electronic circuitry
a base mounted to the housing and including a cavity having opposing tapering sidewalls;
a cap engagable with the base;
an area for receiving a medical electrical lead connector, the lead connector including a plurality of connector elements;
a plurality of electrical contact surfaces held within the cavity, each contact surface of the plurality of contact surfaces defining a portion of a perimeter of the area for receiving the lead connector, and each contact surface located for electrical coupling with a corresponding connector element of the lead connector when the lead connector is inserted within the area;

a plurality of feedthrough wires each electrically coupled to a corresponding contact surface of the plurality of contact surfaces and extending through the base and into the housing for electrical coupling with the circuitry contained therein;

a sealing member held within the base cavity and surrounding the plurality of electrical contact surfaces, the sealing member including at least one interior surface forming another portion of the perimeter of the area for receiving the lead connector, and opposing outer tapered surfaces interfacing with the opposing tapering sidewalls of the cavity;

wherein, when the cap is engaged with the base, the at least one interior surface of the sealing member is compressed about the lead connector inserted within the area.

35. The device of claim 34, wherein the at least one interior surface of the sealing member surrounds a bore, the bore forming a portion of the area for receiving the lead connector.

36. The device of claim 34, wherein the sealing member further includes a plurality of openings, and each contact surface extends into a corresponding opening of the plurality of openings.

37. The device of claim 36, wherein the plurality of contact surfaces are arranged in first and second columns, the first and second columns extending alongside one another.

38. The device of claim 36, wherein the sealing member further includes at least one void, independent of the at least one interior surface and the plurality of openings of the sealing member, the at least one void providing compressible space in a bulk volume of the sealing member.

39. The device of claim 34, further comprising another sealing member attached to the cap, the other sealing member including at least one interior surface further defining the area for receiving the lead connector, and the other sealing member configured to mate with the sealing member held in the base cavity, when the cap is engaged with the base.

40. The device of claim 39, wherein the other sealing member includes opposing outer tapered surfaces interfacing with the opposing tapering sidewalls of the cavity, when the cap is engaged with the base.

* * * * *